United States Patent [19]

Cronje et al.

[11] Patent Number: 4,999,202

[45] Date of Patent: Mar. 12, 1991

[54] COMPOSITION HAVING BACTERIOCIDAL OR BACTERIOSTATIC ACITIVITY

[75] Inventors: Izak J. Cronje, Verwoerdburg; Thomas E. Cloete; Johannes Dekker, both of Pretoria, all of South Africa

[73] Assignee: National Energy Council, Pretoria, South Africa

[21] Appl. No.: 308,674

[22] Filed: Feb. 10, 1989

[30] Foreign Application Priority Data

Feb. 11, 1988 [ZA] South Africa ................. 88/0965

[51] Int. Cl.$^5$ ............................................. A01N 59/06
[52] U.S. Cl. ................................... 424/683; 426/332; 71/77
[58] Field of Search ..................... 424/683; 71/77; 426/332

[56] References Cited

U.S. PATENT DOCUMENTS 3,352,902 11/1967 Moschopedis .................. 260/507

OTHER PUBLICATIONS

Hassett et al CA 106:210835j 1987.
Kalatskaya et al CA 101:18936y 1984.
Oji CA 99:177744r 1983.
Tolpa et al CA 82:111004s 1975.

*Primary Examiner*—Stanley J. Friedman
*Assistant Examiner*—R. Travers
*Attorney, Agent, or Firm*—Cushman, Darby & Cushman

[57] ABSTRACT

A composition which has bacteriocidal or bacteriostatic properties which comprises humic acid or a salt or a derivative thereof as active ingredient in a suitable carrier. The active ingredient is preferably an alkali metal salt of humic acid and the carrier is preferably water.

9 Claims, No Drawings

COMPOSITION HAVING BACTERIOCIDAL OR BACTERIOSTATIC ACITIVITY

BACKGROUND OF THE INVENTION

This invention relates to a composition which has bacteriocidal or bacteriostatic activity.

There is a great demand both in industry and elsewhere for agents which have bacteriocidal activity or bacteriostatic activity or both. An agent which has bacteriocidal activity will destroy bacteria whereas an agent which has bacteriostatic activity will inhibit the growth of bacteria without destroying them. Examples of industrially used bacteriocidal agents are phenol and its derivatives, hypochlorite, mercuric chloride and organic mercury compounds. Many of these agents are specialist chemicals which are expensive. Humic acids occurring naturally in materials such as sewage sludge or decomposed plant material (compost) have been shown in literature to have some anti-microbial action.

Reference to this regard may be had, for example to Hasset et al. Bacteriocidal Action of Humic Acids, *Soil. Biol. Biochem.* 19, 111-113, (1987).

However, due to the divergent origins of these natural sources it is difficult, if not impossible, to produce a uniform and consistent natural humic acid product. It is also difficult and expensive to extract humic acids from these natural sources because of their low humic acid content.

SUMMARY OF THE INVENTION

According to the present invention, there is provided a composition having bacteriocidal or bacteriostatic activity comprising an agent selected from coal-derived humic acid, salts and derivatives thereof, and a suitable carrier.

Further according to the invention, there is provided a method of reducing the bacterial activity of a locus including the step of applying a composition as described above to that locus.

DETAILED DESCRIPTION OF THE INVENTION

Essential to the invention is that the humic acid is derived from coal. Coal, as is known, is a carbonaceous rock originating from plant organic material which has been formed by temperature and pressure, and a variety of chemical processes during a so-called "coalification" period. Preferably, the coal is one with a rank ranging from lignite/brown coal and bituminous hard coal. Coal-derived humic acid has several advantages over humic acid derived from other natural sources, e.g. plant derived organic material.

1. Coal enables humic acid to be produced in a stable form and with uniform and reproducible consistency. Consistency of product is vital for commercial applications. Humic acids derived from natural plant materials or sewage sludge will vary in biological activity due to factors such as their divergent origins and consequent structures.
2. Humic acid derived from coal and its salts and derivatives have been shown to have biocidal efficacy at low concentrations, e.g. 350 ppm. The literature shows that humic acid derived from natural sources does not have biocidal activity or efficacy at such low concentrations.
3. It is difficult to extract humic acids from their natural plant materials and sewage sludge because of low humic acid. Consequently, humic acid derived from such sources is expensive.

Coal-derived humic acid will generally have the following elemental analysis:

| Element | Range (percent) |
| --- | --- |
| Carbon | 45-70 (typically 60-65) |
| Oxygen | 20-40 (typically 25-35) |
| Hydrogen | 2-6 (typically 3-4) |

The coal-derived humic acid will also contain sulphur and nitrogen. The sulphur will generally be present in an amount of up to 5% (typically 0,5-2%) while the nitrogen will generally be present in an amount of 1-2% (typically 1,5%).

Coal-derived humic acid may also be distinguished from humic acid derived from natural sources by the fact that it contains a higher aromaticity and a higher ratio of phenolic to carboxylic groups. By way of example the average ratio of phenolic to carboxylic groups in a coal-derived humic acid is 1,46 in contrast to a ratio of about 1,08 for humic acid derived from a natural plant origin.

The humic acid may be in the form of the free acid or in the form of a salt or other suitable derivative. It is preferable that the humic acid be in the form of a water-soluble salt such as an alkali metal salt.

The composition may take a liquid or solid form, depending on the carrier. When the carrier is liquid, it is preferably an aqueous carrier. In this form, the composition may be used as a household or industrial disinfectant. The composition with an aqueous carrier has been found to be particularly suitable in disinfecting water in cooling towers or the cascade plates over which water in such towers passes. The composition may also be used in the form of a soap or other suitable solid form.

When an aqueous medium is used, the pH of that medium will generally be in the range 2-12, preferably 7-8,5.

The concentration of the agent, in the composition will vary according to the nature of the application. Generally, the concentration of the agent will be in the range 4-25% by weight. For aqueous carriers, the upper limit of the concentration of the humic acid will generally not exceed 17% by weight for at higher concentrations gelling tends to occur.

The composition can be used to reduce the bacterial activity of a locus to which it is applied. The action of the composition will be bacteriocidal at higher concentrations of the agent and bacteriostatic at lower concentrations. In both situations, the bacterial activity of the locus is reduced.

The humic acid will be recovered from coal which has been oxidised. Various oxidation routes for coal have been described in the literature. Some of these processes involve the dry air-oxidation of coal and others involve the wet oxidation of coal.

The humic acid is preferably derived from a coal which has been oxidised by the process described and claimed in European Patent Publication No. 0298710 (Application No. 88306134.3). The method of this European Patent Publication involves mixing coal with an aqueous medium to produce a slurry having a pH in the range of 4-9, reacting the slurry with a gaseous oxidant selected from oxygen, air and mixtures thereof under conditions of temperature and pressure and for a period to cause the oxidation of coal thereby producing oxidised coal containing humic acids, and separating the oxidised coal containing humic acid from the aqueous medium. This process has the particular advantage that it achieves high humic acid yields and selectivity.

The humic acid may be recovered from the oxidised coal by extraction with aqueous alkali. This produces a solution containing the humic acid in the form of a soluble alkali salt. The free humic acid may be generated from such solutions by acidification.

The invention will be illustrated by the following non-limiting examples. The first example describes a particular method of producing humic acid. The second example describes certain efficacy studies carried out using humic acid.

EXAMPLE 1

20 g of a South African coal with a mean particle size of 10 microns was slurried in 400 ml water and quantitatively transferred to a stirred autoclave of 2 liter capacity. The autoclave was charged with oxygen to a pressure of 4,0 MPa (cold) and sealed.

The turbine stirrer, running at 1500 rpm, and the bar type heaters were simultaneously started. The temperature was controlled at 150° C.±2° C. for the desired period after which the reaction was terminated by cooling the reactor with a jet of compressed air and allowing the pressure to drop to atmospheric, by opening a valve.

The humic acid content of the oxidised coal was then determined as follows: The coal slurry, quantitatively transferred to a round bottom flask, was mixed with 20 g of sodium hydroxide pellets and refluxed for five hours after which the reaction mixture was cooled and centrifuged to separate the residue.

The residue was washed twice with 0,1N NaOH solution and twice with water. All the washings were added to the solution obtained after centrifuging. The residue was dried, weighed and the organic content determined.

The humic acid contained in the solution was recovered by precipitation, after acidification with hydrochloric acid to a pH value of 2. The now insoluble humic acid was centrifuged, washed with 0,1N HCl solution and water. After drying to constant mass the solid humic acid was weighed and analysed for organic content.

Summary of reaction conditions:

| Temperature | 150° C. |
|---|---|
| Oxygen partial pressure | 4,0 MPa (cold) |
| Slurry concentration | 5% |

The result obtained are tabulated below:

| Reaction period (minutes) | C recovered as % humic acid |
|---|---|
| 60 | 45,5 |
| 120 | 52,5 |
| 180 | 63,5 |
| 240 | 45,7 |

The humic acid figures relate to the carbon content of the starting coal.

The elemental analysis of the humic acid was as follows:

| Element | Percent |
|---|---|
| Carbon | 63,3 |
| Oxygen | 31,3 |
| Hydrogen | 3,4 |
| Sulphur | 0,4 |
| Nitrogen | 1,6 |

EXAMPLE 2

The ability of coal-derived humic acid as produced by Example 1 to inhibit the growth of bacteria was examined. The typical procedure followed was as follows:

Three Erlenmyer flasks equipped with side-arms were filled with a sterile growth medium (nutrient broth). All the media in the flasks were inoculated with the organism on which the effect of humic acid was being evaluated. To two flasks of humic acid were added to obtain concentrations of 0,01% and 0,1% (on a mass per volume basis) humic acid, respectively. The addition of humic acid was omitted to the third flask with the intention to use it as a control. The flasks were incubated at 27° C. and the growth of the organism was monitored by reading the absorbance at 540 nm in an ultra violet/visible spectrophotometer during the incubation period.

Abovementioned procedure was done in duplicate for every organism tested. The following five organisms, i.e. bacteria selected to cover a large spectrum, were tested:

*Pseudomonas aeruginosa*
*Staphylococcus aureus*
*Escherichia coli*
*Bacillis subtillis*
*Acinetobacter calcoaceticus*

The results obtained were as follows:

(a) With *P. aeruginosa*

The period needed for the control's organisms to double in number (flask containing growth medium and organism but no humic acid) was determined to be 2,4 hours. In the flasks containing 0,01% m/v humic acid and 0,1% m/v humic acid the periods needed to double the number of organisms were found to be 8,6 and 11,55 hours respectively.

Thus, concentrations of both 0,1% and 0,01% m/v humic acid exhibited an inhibitory effect under ideal conditions for growth on *P. aeruginosa*.

(b) With *S. aureus*

The periods needed for the organisms to double in number in the control medium and media containing 0,01% and 0,1% m/v humic acid were found to be 1,22, 1,68 and 8,21 hours respectively.

Thus, humic acid at a concentration of 0,1% m/v inhibited the growth of *S. aureus* under ideal conditions for growth.

(c) With *E. coli*

The periods needed for the organisms to double in number in the control medium and media containing 0,01% and 0,1% m/v humic acid were found to be 1,28, 1,58 and 4,06 hours respectively.

Thus, humic acid at a concentration of 0,1% inhibited growth of *E. coli* under ideal conditions for growth.

(d) With *B. subtillis*

The periods needed for the organisms to double in number in the control medium and the medium containing 0,01% m/v humic acid were found to be 1,79 and 3,07 hours respectively.

No definite conclusion can be drawn as no result for a medium containing 0,1% m/v humic acid was obtained.

(e) With *A. calcoaceticus*

The periods needed for the organisms to double in number in the control medium and media containing 0,01% and 0,1% m/v humic acid were found to to 2,87, 2,54 and 12,15 hours respectively.

Thus, humic acid, at a concentration of 0,1% m/v, inhibited growth of *A. calcoaceticus* under ideal conditions for growth.

EXAMPLE 3

The efficacy of coal-derived humic acid as produced by Example 1 was compared with naturally occurring sewage sludge humic acid.

METHODOLOGY

Test organisms:
*Klebsiella pneumoniae*
*Pseudomonas aeruginosa*
*P Fluorescens*
*B cereus*
*A calcosceticus*

BIOCIDE USED

Coal-derived humic acid concentration: 350 ppm.

The test organisms were exposed to the above humic acid concentration for 6 hours. The initial bacterial number was determined and again 6 hours after the addition of the humic acid. The percentage kill was calculated as follows:

$$\% \text{ Kill} = 100 - \left(\frac{\text{survivor count}}{\text{initial count}}\right) \times 100$$

RESULTS

TABLE 1

The effect of humic acid on the test organisms

| Test organism | % Kill |
|---|---|
| *P fluorescens* | 86 |
| *P aeruginosa* | 85 |
| *B cereus* | 96 |
| *A calcoacelicus* | 66 |
| *Klebsiella pneumoniae* | 99 |

By comparing the results in Table 1, with published data (Hassett, et al *Soil. Biol. Biochem.* 19, 111–113, (1987)), it is clear that the humic acids derived from coal were significantly more effective than humic acid derived from plant sources. A much lower concentration i.e. 350 ppm -vs-700 ppm gave a better kill percentage (86%) in 6 hours than that obtained with natural humic acids (obtained from sewage sludge) over a period of 24 hours.

We claim:

1. A composition having bacteriocidal or bacteriostatic activity comprising an agent selected from oxidized coal derived humic acid, and salts thereof, and a suitable carrier, wherein the oxidized coal derived humic acid contains at least the following elements:

| Element | Range (percent) |
|---|---|
| Carbon | 45–70 |
| Oxygen | 20–40 |
| Hydrogen | 2–6 |

2. A composition according to claim 1 wherein the coal-derived humic acid also includes the following elements:

| Element | Range (percent) |
|---|---|
| Sulphur | up to 5 |
| Nitrogen | 1–2 |

3. A composition according to claim 1 wherein the agent is an alkali metal salt of coal-derived humic acid.

4. A composition according to claim 1 wherein the carrier is a liquid carrier.

5. A composition according to claim 3 wherein the liquid carrier is an aqueous carrier.

6. A composition according to claim 1 wherein the concentration of the agent is in the range 4 to 25 percent by weight.

7. A composition according to claim 1 wherein the concentration of the agent is in the range 4 to 17 percent by weight.

8. A method of reducing the bacterial activity at a locus comprising applying an effective amount of a composition according to claim 1 to that locus.

9. A method according to claim 7 wherein the locus is an aqueous medium.

* * * * *